(12) United States Patent
Naya et al.

(10) Patent No.: US 8,268,613 B2
(45) Date of Patent: Sep. 18, 2012

(54) SURFACE PLASMON RESONANCE MEASURING CHIP AND METHOD OF MANUFACTURE THEREOF

(75) Inventors: Masayuki Naya, Kaisei-machi (JP); Takashi Kubo, Kaisei-machi (JP); Takashi Ito, Saitama-ken (JP); Yoshimitsu Nomura, Saitama-ken (JP)

(73) Assignees: Fujinon Corporation, Saitama (JP); FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/761,221

(22) Filed: Apr. 15, 2010

(65) Prior Publication Data

US 2010/0195107 A1  Aug. 5, 2010

Related U.S. Application Data

(63) Continuation of application No. 10/053,585, filed on Jan. 24, 2002, now abandoned.

(30) Foreign Application Priority Data

Jan. 25, 2001 (JP) ................. 2001-016632
Sep. 28, 2001 (JP) ................. 2001-299568

(51) Int. Cl.
*C12M 1/34* (2006.01)
(52) U.S. Cl. ....... 435/288.7; 385/12; 385/129; 385/130; 422/82.11; 435/808; 436/164; 436/525; 436/805
(58) Field of Classification Search .................. None
See application file for complete search history.

(56) References Cited

U.S. PATENT DOCUMENTS

| 4,844,613 | A |   | 7/1989 | Batchelder et al. |
| 5,492,840 | A |   | 2/1996 | Malmqvist et al. |
| 5,965,456 | A | * | 10/1999 | Malmqvist et al. ........... 436/514 |
| 6,104,484 | A |   | 8/2000 | Nagata et al. |
| 6,268,125 | B1 | * | 7/2001 | Perkins .............. 435/5 |

(Continued)

FOREIGN PATENT DOCUMENTS

EP  0 936 227 A1  8/1999

(Continued)

OTHER PUBLICATIONS

Ueno et al., "A Waveguide SPR Sensor," PHS-00-9, Sep. 22, 2000, pp. 13-16, in Japanese with English abstract.

(Continued)

*Primary Examiner* — Chris L Chin
(74) *Attorney, Agent, or Firm* — Sughrue Mion, PLLC

(57) ABSTRACT

A surface plasmon resonance measuring apparatus is provided with a dielectric block, a metal film formed on a surface of the dielectric block, a light source for emitting a light beam, an optical system for making the light beam enter the dielectric block at various angles of incidence so that a condition for total internal reflection is satisfied at an interface between the dielectric block and the thin film layer, and a photodetector for detecting the intensity of the light beam satisfying total internal reflection at the interface. In the measurement chip to be utilized in the surface plasmon resonance measuring apparatus, the dielectric block is formed from a synthetic resin in which, when said light beam is p-polarized outside said dielectric block and then strikes the interface, the intensity of a s-polarized component at the interface is 50% or less of the intensity of the light beam at the interface.

8 Claims, 15 Drawing Sheets

U.S. PATENT DOCUMENTS

| | | |
|---|---|---|
| 6,597,456 B2 | 7/2003 | Kubo et al. |
| 6,611,367 B1 | 8/2003 | Naya et al. |
| 6,795,192 B2 | 9/2004 | Dickopf et al. |
| 7,037,727 B1 * | 5/2006 | Miura et al. ............ 436/518 |
| 7,205,155 B1 | 4/2007 | Schawaller et al. |

FOREIGN PATENT DOCUMENTS

| | | |
|---|---|---|
| EP | 1 186 881 A1 | 3/2002 |
| JP | 62-083121 A | 4/1987 |
| JP | 6-167443 A | 6/1994 |
| JP | 07-043523 U | 8/1995 |
| JP | 09-207178 A | 8/1997 |
| JP | 09-257695 A | 10/1997 |
| JP | 09-257699 A | 10/1997 |
| JP | 09-257701 A | 10/1997 |
| JP | 10-300667 A | 11/1998 |
| JP | 11-029526 A | 2/1999 |
| JP | 11-037922 A | 2/1999 |
| JP | 11-037934 A | 2/1999 |
| JP | 11-271218 A | 10/1999 |
| JP | 11-271307 A | 10/1999 |
| JP | 2000-178317 A | 6/2000 |
| JP | 2000-212125 A | 8/2000 |
| JP | 2002-296177 A | 10/2002 |
| WO | 98/55231 A1 | 12/1998 |
| WO | 01/14859 A1 | 3/2001 |
| WO | 01/63257 A1 | 8/2001 |
| WO | 01/69207 A1 | 9/2001 |
| WO | 99/60382 A1 | 11/2009 |

OTHER PUBLICATIONS

Meléndez et al. (previously identified as Carr et al.), "Development of a surface plasmon resonance sensor for commercial applications," Sensors and Actuators B, vol. 39, No. 1-3, Mar. 1, 1997, pp. 375-379.

Natsuume et al., "A New High Heat Resistant, High Clarity, and High Humidity Resistant Polymer for Optical Uses," Materials Research Society Symposium Proceedings, vol. 150, Apr. 25, 1989, pp. 245-250, XP009007850.

Jorgenson, "A surface plasmon resonance side active retro-reflecting sensor," Sensors and Actuators B, vol. 73, No. 2-3, Mar. 10, 2001, pp. 236-248.

EP Communication, dated Apr. 6, 2004, issued in corresponding EP Application No. 02001783.6, 6 pages.

Notice of Grounds for Rejection, dated Jul. 20, 2010, issued in corresponding JP Application No. 2001-299568, 4 pages in English and Japanese.

Notice of Grounds for Rejection, dated Nov. 24, 2010, issued in corresponding JP Application No. 2001-299568, 4 pages in English and Japanese.

* cited by examiner

F I G. 12A  F I G. 12B
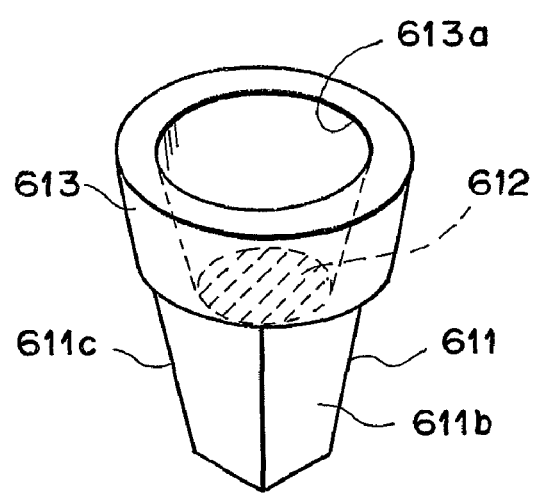 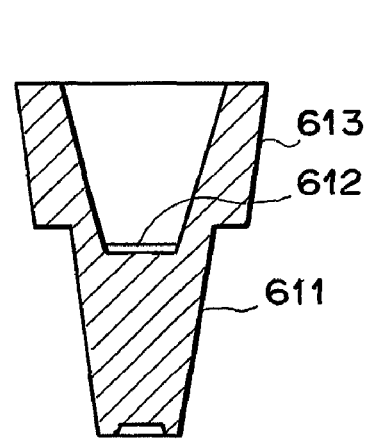

F I G. 13
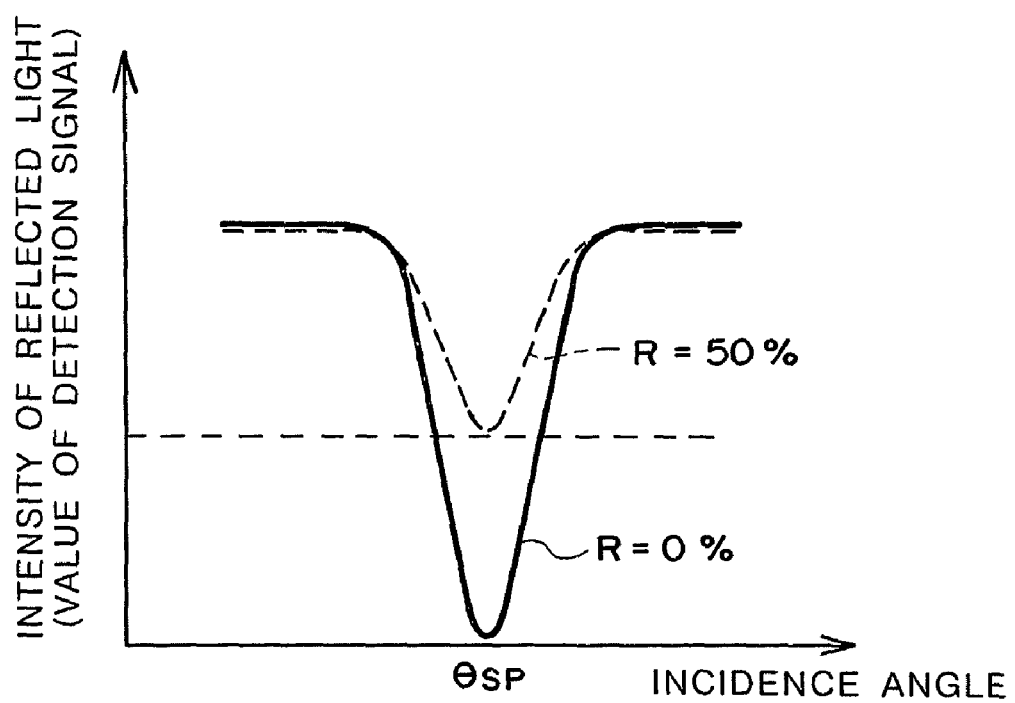

F I G. 14A
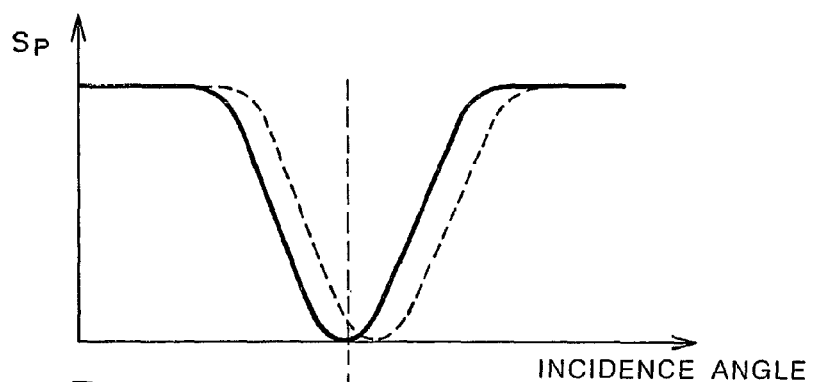
F I G. 14B
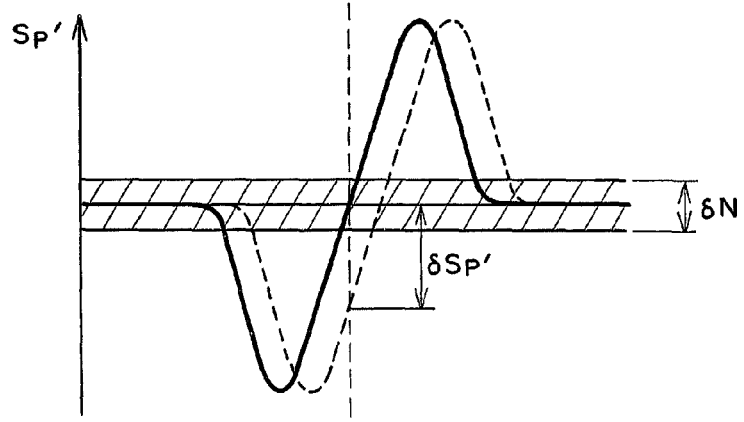

F I G. 15A
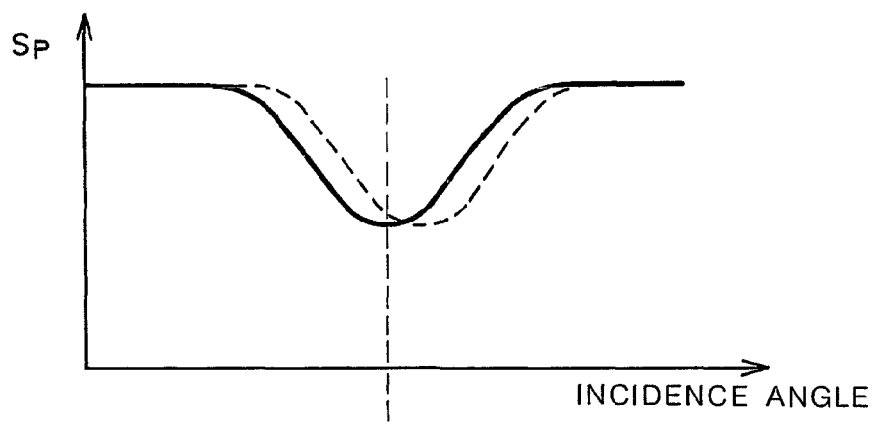
F I G. 15B
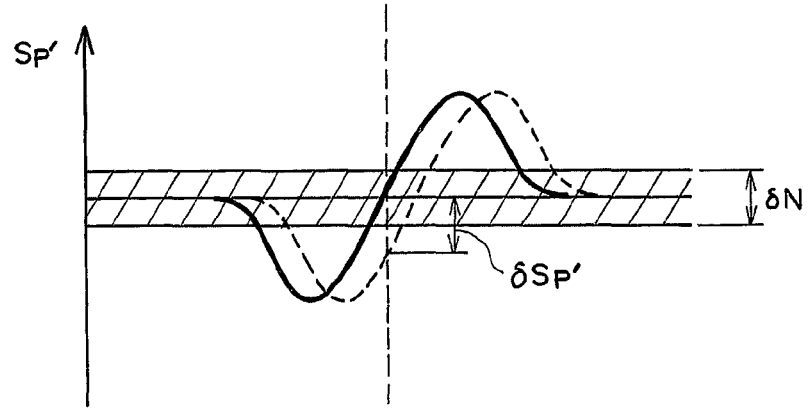

SURFACE PLASMON RESONANCE MEASURING CHIP AND METHOD OF MANUFACTURE THEREOF

This application is a continuation of U.S. application Ser. No. 10/053,585, filed Jan. 24, 2002, which claims priority to JP 2001-016632, filed Jan. 25, 2001, and JP 2001-299568, filed Sep. 28, 2001, each of which is incorporated by reference in its entirety.

BACKGROUND OF THE INVENTION

1. Field of the Invention

The present invention relates to a measuring chip that is employed in a surface plasmon resonance measuring apparatus for quantitatively analyzing a substance in a sample by utilizing the excitation of a surface plasmon. The present invention also relates to a method of manufacture of a measuring chip as described above.

2. Description of the Related Art

In metals, if free electrons are caused to vibrate in a group, compression waves called plasma waves will be generated. The compression waves generated in a metal surface and quantized are called surface plasmon.

A variety of surface plasmon resonance measuring apparatuses have been proposed to quantitatively analyze a substance in a sample by taking advantage of a phenomenon that surface plasmon is exited by light waves. Among the apparatuses, an apparatus employing a system called "Kretschmann configuration" is particularly well known (e.g., see Japanese Unexamined Patent Publication No. 6 (1994)-167443).

The surface plasmon resonance measuring apparatus employing the "Kretschmann configuration" is equipped mainly with a dielectric block formed, for example, into the shape of a prism; a metal film, formed on a surface of the dielectric block, for placing a sample thereon; a light source for emitting a light beam; an optical system for making the light beam enter the dielectric block so that a condition for total internal reflection is satisfied at the interface between the dielectric block and the metal film and that various angles of incidence, including a surface plasmon resonance condition, are obtained; and photodetection means for measuring the intensity of the light beam satisfying total internal reflection at the interface to detect surface plasmon resonance.

In order to obtain various angles of incidence in the aforementioned manner, a relatively thin light beam may be caused to strike the above-mentioned interface at different angles of incidence, or relatively thick convergent or divergent rays may be caused to strike the interface so that they contain components incident at various angles. In the former, a light beam whose reflection angle varies with deflection of the light beam, can be detected by a small photodetector that is moved in synchronization with the light beam deflection, or by an area sensor extending in the direction where the angle of reflection varies. In the latter, on the other hand, rays reflected at various angles can be detected by an area sensor extending in a direction where all the reflected rays can be received.

In the surface plasmon resonance measuring apparatus mentioned above, if a light beam strikes the metal film at a specific incidence angle $\theta_{sp}$ equal to or greater than a critical angle of incidence at which total internal reflection takes place, evanescent waves having electric field distribution are generated in the sample in contact with the metal film, whereby surface plasmon is excited at the interface between the metal film and the sample. When the wave vector of the evanescent light is equal to the wave number of the surface plasmon and therefore the wave numbers between the two are matched, the evanescent waves and the surface plasmon resonate and light energy is transferred to the surface plasmon, whereby the intensity of light satisfying total internal reflection at the interface between the dielectric block and the metal film drops sharply. The sharp intensity drop is generally detected as a dark line by the above-mentioned photodetection means.

Note that the above-mentioned resonance occurs only when the incident light beam is a p-polarized light beam. Therefore, in order to make the resonance occur, it is necessary that a light beam be p-polarized before it strikes the interface.

If the wave number of the surface plasmon is found from a specific incidence angle $\theta_{sp}$ at which attenuated total reflection (hereinafter referred to as ATR) takes place, the dielectric constant of a sample to be analyzed can be calculated by the following Equation:

$$K_{sp}(\omega) = (\omega/C)\{\in_m(\omega)\in_s\}^{1/2}/\{\in_m(\omega)+\in_s\}^{1/2}$$

where $K_{sp}$ represents the wave number of the surface plasmon, $\omega$ represents the angular frequency of the surface plasmon, c represents the speed of light in vacuum, and $\in_m$ and $\in_s$ represent the dielectric constants of the metal and the sample, respectively.

If the dielectric constant $\in_s$ of the sample is found, the density of a specific substance in the sample is found based on a predetermined calibration curve, etc. As a result, the specific substance can be quantitatively analyzed by finding the incidence angle $\theta_{sp}$ at which the intensity of reflected light drops.

In the conventional surface plasmon resonance measuring apparatus employing the aforementioned system, the metal film on which a sample is placed must be exchanged for a new one each time a measurement is made. Because of this, the metal film is fixed to a first dielectric block in the form of a plate, and a second dielectric block in the form of a prism is provided as an optical coupler for making the aforementioned total internal reflection occur. The first dielectric block is united with a surface of the second dielectric block. The second dielectric block is fixed with respect to an optical system, and the first dielectric block and the metal film are used as a measuring chip. In this manner, the measuring chip can be exchanged for a new one, every time a measurement is made.

However, in the case where the conventional exchangeable measuring chip is employed, a gap occurs between the first dielectric block and the second dielectric block and the refractive index becomes discontinuous. To prevent the discontinuity, it is necessary that the two dielectric blocks be united through an index-matching solution. The operation of uniting the two dielectric blocks in a body is fairly difficult, and consequently, the conventional measuring chip is not easy to handle in making a measurement. Particularly, in the case where measurement is automated by automatically loading a measuring chip into a turret, then rotating the turret, and automatically supplying the measuring chip to a measuring position where a light beam enters the measuring chip, the loading and removal of the measuring chip is time-consuming, resulting in a reduction in the efficiency of the automatic measurement.

In addition, there is a possibility that the conventional measuring chip will have a detrimental influence on the environment, because it uses an index-matching solution.

In view of the circumstances mentioned above, the applicant has proposed a surface plasmon resonance measuring chip that can be easily exchanged for a new one without requiring an index-matching solution (Japanese Unexamined Patent Publication No. 2000-212125).

This surface plasmon resonance measuring chip is equipped with a dielectric block; a metal film, formed on a surface of the dielectric block, for placing a sample thereon; a light source for emitting a light beam; an optical system for making the light beam enter the dielectric block at various angles of incidence so that a condition for total internal reflection is satisfied at an interface between the dielectric block and the metal film; and photodetection means for detecting the intensity of the light beam satisfying total internal reflection at the interface to detect surface plasmon resonance. The dielectric block is formed as a single block that includes an entrance surface which the light beam enters, an exit surface from which the light beam emerges, and a surface on which the metal film is formed. The metal film is united with the dielectric block.

In the surface plasmon resonance measuring chip disclosed in the aforementioned publication No. 2000-212125, the dielectric block is formed as a single block that includes an entrance surface which the light beam enters, an exit surface from which the light beam emerges, and a surface on which the metal film is formed (this block also functions as an optical coupler because it includes an entrance surface and an exit surface), and the dielectric block is united with the metal film. Therefore, if only the measuring chip is installed in and removed from the optical system, the measuring chip can be easily exchanged for a new one.

That is, since the surface plasmon resonance measuring chip does not require the aforementioned two dielectric blocks, the measuring chip does not have to employ an index-matching solution through which the two dielectric blocks are united. Thus, the measuring chip is capable of eliminating the inconvenience of handling that is caused by employing an index-matching solution.

In addition, if the measuring chip does not need to employ an index-matching solution, the measuring chip is prevented from having a detrimental influence on the environment.

Note that desirable materials for the dielectric block are glass and synthetic resin. Particularly, synthetic resin is advantageous in that measuring chips can be manufactured at low costs by injection molding.

However, in the case where measuring chips are formed from synthetic resin, the problem of a reduction in the signal-to-noise (S/N) ratio for the output signal of the photodetection means that detects surface plasmon resonance will arise.

SUMMARY OF THE INVENTION

The present invention has been made in view of the circumstances mentioned above. Accordingly, it is the primary object of the present invention to provide a measuring chip, consisting of synthetic resin, which is capable of realizing high accuracy of measurement by assuring a high S/N ratio for the output signal of photodetection means that detects surface plasmon resonance.

It is another object of the present invention to provide a method of manufacture of a surface plasmon resonance measuring chip as described above.

To achieve this end and in accordance with an important aspect of the present invention, there is provided a surface plasmon resonance measuring chip comprising: (1) a dielectric block; (2) a metal film, formed on a surface of the dielectric block, for placing a sample thereon; (3) a light source for emitting a light beam; (4) an optical system for making the light beam enter the dielectric block at various angles of incidence so that a condition for total internal reflection is satisfied at an interface between the dielectric block and the metal film; and (5) photodetection means for detecting the intensity of the light beam satisfying total internal reflection at the interface to detect surface plasmon resonance. In the surface plasmon resonance measuring chip, the dielectric block is formed as a single block that includes an entrance surface which the light beam enters, an exit surface from which the light beam emerges, and a surface on which the metal film is formed. The metal film is united with the dielectric block. Furthermore, the dielectric block is formed from a synthetic resin in which, when the light beam is p-polarized outside the dielectric block and then strikes the interface, the intensity of a s-polarized component at the interface is 50% or less of the intensity of the light beam at the interface. That is, the conversion ratio of the p-polarized component to the s-polarized component is 50% or less. Hereinafter, this conversion ratio will be referred to as "conversion ratio R".

In a preferred form of the present invention, the aforementioned dielectric block is formed from a synthetic resin in which, when the light beam is p-polarized outside the dielectric block and then strikes the interface, the intensity of a s-polarized component at the interface is 30% or less of the intensity of the light beam at the interface, and further desirably 10% or less of the intensity of the light beam at the interface. synthetic resin. In the surface plasmon resonance measuring chip of the present invention, synthetic resin a synthetic resin that suppresses the intensity of the s-polarized component of the light beam may be, for example, PMMA (polymethylmethacrylate).

In the surface plasmon resonance measuring chip of the present invention, it is desirable that a sensing medium that exhibits a coupling reaction with a specific substance in the sample is fixed on the metal film.

It is desirable that the surface plasmon resonance measuring chip be provided with a sample holding mechanism for holding a sample on the metal film. More specifically, the sample holding mechanism is constructed of a member having a hole in which the metal film is received. The cross section of the hole of the member is tapered so that it gradually increases in size from the bottom of the hole toward the top of the hole.

In the surface plasmon resonance measuring chip, it is desirable that the aforementioned dielectric block have a polygonal cross section (such as a square cross section, etc.) which gradually increases in size from the bottom of the block toward the top of the block.

The method of manufacture of the surface plasmon resonance measuring chip according to the present invention is a method of manufacture of a surface plasmon resonance measuring chip having the basic structure as that disclosed in the aforementioned Japanese Unexamined Patent Publication No. 2000-212125. That is, it is a method of manufacturing a surface plasmon resonance measuring chip for use in a surface plasmon resonance measurement apparatus constituted of: a light source for emitting a light beam; an optical system for making said light beam enter a dielectric block at various angles of incidence so that a condition for total internal reflection is satisfied at an interface between said dielectric block and said metal film; and photodetection means for detecting the intensity of said light beam satisfying total internal reflection at said interface to detect surface plasmon resonance; wherein said dielectric block is formed as a single block that includes an entrance surface which said light beam enters, an exit surface from which said light beam emerges, and a surface on which said metal film is formed; comprising the step of: manufacturing the measuring chip with said dielectric block being formed integrally with said metal film by positioning a resin introducing gate in a position that faces the surface of the mold that defines the surface on which said metal film is to be formed and forming said block by injection molding.

The inventors have made various investigations and experiments and found that in the conventional surface plasmon resonance measuring chip employing synthetic resin material, the problem of a reduction in the S/N ratio for the output signal of the photodetection means for detecting surface plasmon resonance results from a change in the polarized component of a light beam caused by optical distortion (double refraction, etc.) generated in the synthetic resin material.

That is, even if a light beam is p-polarized and is caused to strike the interface between a synthetic resin dielectric block and a metal film to generate surface plasmon resonance, the polarization state of the light beam will change due to the optical distortion (double refraction, etc.) of the synthetic resin, as the light beam travels through the synthetic resin dielectric block. For this reason, when the light beam reaches the interface, a strong s-polarized component has often been generated. The s-polarized component makes no contribution to surface plasmon resonance, and the s-polarized component always satisfies total internal reflection at the interface and is detected as a bias component by the photodetection means. Because of this, the light quantity of the p-polarized component which causes ATR to occur is reduced and the S/N ratio for the detected signal is reduced.

This point will be described in greater detail below. FIG. 13 is a graph that shows the relationship between the incidence angle of light that enters the interface between a dielectric block and a metal film in a surface plasmon resonance measuring apparatus; and the intensity of detected total internally reflected light. In the figure, the solid and broken lines represent a case in which 100% of the p-polarized component of the p-polarized light beam that enters the dielectric block is preserved when the light reaches the interface between the dielectric block and the metal film (that is, the conversion ratio R is 0%), and a case in which 50% of the p-polarized component of the p-polarized light beam that enters the dielectric block is preserved when the light reaches the interface between the dielectric block and the metal film (that is, the conversion ratio R is 50%), respectively. As described above, with regard to surface plasmon resonance measurement, basically, what is sought is the dielectric constant of the sample from the incidence angle $\theta_{sp}$ at which ATR occurs, or the nature of the sample corresponding to this dielectric constant. Thus, the deeper the dip (drop) of the detected total internal reflection signal for the incidence angle $\theta_{sp}$, the higher the S/N ratio of the detection signal obtained. As shown in the figure, in the case that the conversion ratio R is 50%, the depth of the dip is ½ that of the case that the conversion ratio R is 0%. As the noise level is constant for both cases, the S/N ratio of the detection signal is also ½. In this manner, the S/N ratio of the detection signal is affected by the conversion ratio R of the light beam to the s-polarized component.

Based on the facts described above, the present inventors experimentally investigated to what degree the conversion ratio R had to be suppressed in order to make practical surface plasmon resonance measurement possible, when attempting to make a light beam incident on the interface between a dielectric block and a metal film in a p-polarized state. With regard to the experiments, a surface plasmon resonance measuring apparatus as shown in FIG. 1, to be described later, was employed. The S/N ratio was evaluated based on a differential signal, obtained by differentiating the output signal (SPR signal) of a photodetector for detecting the intensity of totally internally reflected light. Note that with regard to this apparatus, the noise level of the electrical system for detecting the intensity of totally internally reflected light is approximately 1 mV. This is a noise level common to electrical circuits.

With reference to FIG. 14, the method of deriving the S/N ratio in this case will be described. In the figure, A and B represent the aforementioned SPR signal Sp and the differential signal Sp' differentiated therefrom, respectively, for a case in which the conversion ratio R is 0%. In addition, a sensing medium that exhibits a coupling reaction with a specific substance in the sample is placed on the metal film. The solid lines and the broken lines in the figures represent the signal values before and after the coupling reaction, respectively. The case in which the dielectric constant of the specific substance, that is, the identity of the specific substance which exhibited the coupling reaction with the sensing medium, is sought from the amount of change $\delta Sp'$ of the differential signal Sp' before and after the coupling reaction, will be considered.

In this case, if the noise level is set as $\delta N$, then S/N= $(\delta Sp'/\delta N)$. Incidentally, in the case that the conversion ratio R is 50%, the SPR signal and the differential signal thereof will be those shown in FIG. 15A and FIG. 15B, respectively. As can be seen by a comparison of FIG. 14 and FIG. 15, while the noise level $\delta N$ is constant, as the amount of change $\delta Sp'$ of the differential signal Sp' in the case in which the conversion ratio R is 50% is ½ that in the case in which the conversion ratio R is 0%, the S/N ratio of the case in which the conversion ratio R is 50% is also ½ that in the case in which the conversion ratio R is 0%.

By deriving the S/N ratio in the manner described above, experiments were conducted to investigate to what degree the conversion ratio R should be suppressed in order to realize a S/N ratio greater than or equal to 10, which is the S/N ratio generally required to perform this type of measurement accurately. With regard to the experiments, the conversion ratio R was set to various values, and investigation was conducted for each case. However, only the conversion ratios R relating to the present invention will be described below.

(1) Conversion Ratio R=50%

In this case, when the change in refractive index was $1 \times 10^{-5}$, the amount of change $\delta Sp'$ of the differential signal Sp' became approximately 5.6 mV. As the noise level is approximately 1 mV as described above, the change in refractive index at which S/N=10 becomes $1.8 \times 10^{-5}$. This value is substantially equal to that obtained in, for example, the screening of drugs, when the aforementioned sensing medium couples with a substance having a low molecular weight of 360. As the majority of low molecular weight substances subject to drug screening have a molecular weight on the order of 360~800 (for example, biotinylated amine has a molecular weight of 374), if a dielectric block is formed by a synthetic resin with a conversion ratio R of less than or equal to 50%, low molecular weight substances such as these can be screened for with high accuracy.

(2) Conversion Ratio R=30%

In this case, when the change in refractive index was $1 \times 10^{-5}$, the amount of change $\delta Sp'$ of the differential signal Sp' became approximately 7.8 mV. As the noise level is approximately 1 mV as described above, the change in refractive index at which S/N=10 becomes $1.3 \times 10^{-5}$. This value is substantially equal to that obtained when the aforementioned sensing medium couples with a substance having a low molecular weight of 260. As there exist a number of substances from among the of low molecular weight substances subject to drug screening having a molecular weight on the order of 260~360 (for example, vitamin B1 has a molecular weight of 334), if a dielectric block is formed by a synthetic resin with a conversion ratio R of less than or equal to 30%, low molecular weight substances such as these can be screened for with high accuracy.

(3) Conversion Ratio=10%

In this case, when the change in refractive index was $1 \times 10^{-5}$, the amount of change $\delta Sp'$ of the differential signal $Sp'$ became approximately 10 mV. As the noise level is approximately 1 mV as described above, S/N ratio equals 10 at this change in refractive index. This value is substantially equal to that obtained when the aforementioned sensing medium couples with a substance having a low molecular weight of 200. In drug screening, it is said that if substances having a molecular weight greater than or equal to 200 are detectable, it is possible to screen for substantially all substances (for example, biotin has a molecular weight of 244). Therefore, if a dielectric block is formed by a synthetic resin with a conversion ratio R of less than or equal to 10%, the apparatus becomes applicable to the screening of various drugs.

Whether or not the aforementioned polarization ratio has been maintained can be judged by detecting a polarization ratio from the dielectric block. That is, the influence of optical distortion on the polarization state of the light is greater at the exit surface of the dielectric block than at the interface. Therefore, if the polarization ratio for the emergent light satisfies the aforementioned condition, a change in the polarization state at the interface due to the influence of optical distortion is less than that.

In the present invention, the aforementioned sample holding mechanism is provided to hold a sample on the metal film; the sample holding mechanism consists of a member having a hole; and furthermore, the hole is tapered to that the cross section thereof increases in size from the bottom of the dielectric block toward the top of the dielectric block. In this case, the effect of making the thickness of the metal film even can also be obtained. That is, the metal film is generally formed by vapor deposition. If the sample holding mechanism is formed into a shape such as that described above, a deposited metal film is held in the hole of the sample holding mechanism and can be prevented from becoming uneven in thickness.

In the surface plasmon resonance measuring chip, when the aforementioned dielectric block has a polygonal cross section (such as a square cross section, etc.) which gradually increases in size from the bottom of the block toward the top of the block, positioning in installing this chip in the measuring apparatus is facilitated.

That is, if a polygonal bore (a square bore, etc.) is formed in the horizontal measuring table, etc., of the measuring apparatus, and the polygonal dielectric block is fitted in the polygonal bore, the dielectric block is automatically set in a predetermined direction within a horizontal plane, because the polygonal portions engage with each other. Thus, there is no possibility that the measuring chip will be shifted horizontally from the polygonal bore.

Furthermore, if the tapered polygonal dielectric block is inserted into the polygonal bore formed in the measuring table, etc., the dielectric block is automatically stopped at a vertical position where the polygonal portions engage with each other. Thus, vertical positioning is also easily performed.

If the method of manufacture of a surface plasmon resonance measuring chip of the present invention is applied, a measuring chip having comparative intensities of the s-polarized component (conversion ratio R) of less than or equal to 50%, less than or equal than 30%, and less than or equal to 10% can be obtained. This is thought to be because the polarization state of the light beam incident on the surface on which the metal film is formed is preserved. This is accomplished by positioning a resin introducing gate in a position that faces the surface of the mold that defines the surface on which said metal film is to be formed and forming said block by injection molding, thereby improving the planarity of said surface.

BRIEF DESCRIPTION OF THE DRAWINGS

The present invention will be described in further detail with reference to the accompanying drawings wherein:

FIG. 12A is a perspective view showing a surface plasmon resonance measuring chip constructed according to an eighth embodiment of the present invention;

FIG. 12B is a sectional side view showing the surface plasmon resonance measuring chip of FIG. 12A;

FIG. 13 is a graph that shows the relationship between the incidence angle of light that enters the interface between a dielectric block and a metal film in a surface plasmon resonance measuring apparatus;

FIG. 14A is a graph that shows the change in the output signal of the photodetector corresponding to the refractive index of the sample;

FIG. 14B is a graph that shows the change in the differential signal, differentiated from the output signal of the photodetector, corresponding to the refractive index of the sample;

FIG. 15A is a graph that shows the change in the output signal of the photodetector corresponding to the refractive index of the sample when the dielectric block is formed from a material different from that in FIG. 14A;

FIG. 15B is a graph that shows the change in the differential signal, differentiated from the output signal of the photodetector, corresponding to the refractive index of the sample when the dielectric block is formed from a material different from that in FIG. 14B;

DESCRIPTION OF THE PREFERRED EMBODIMENTS

Referring now in greater detail to the drawings and initially to FIGS. 1 to 3, there is shown a surface plasmon resonance measuring apparatus that employs a surface plasmon resonance measuring chip (hereinafter referred to as a measuring chip) 10 constructed according to a first embodiment of the present invention.

Figure 1:
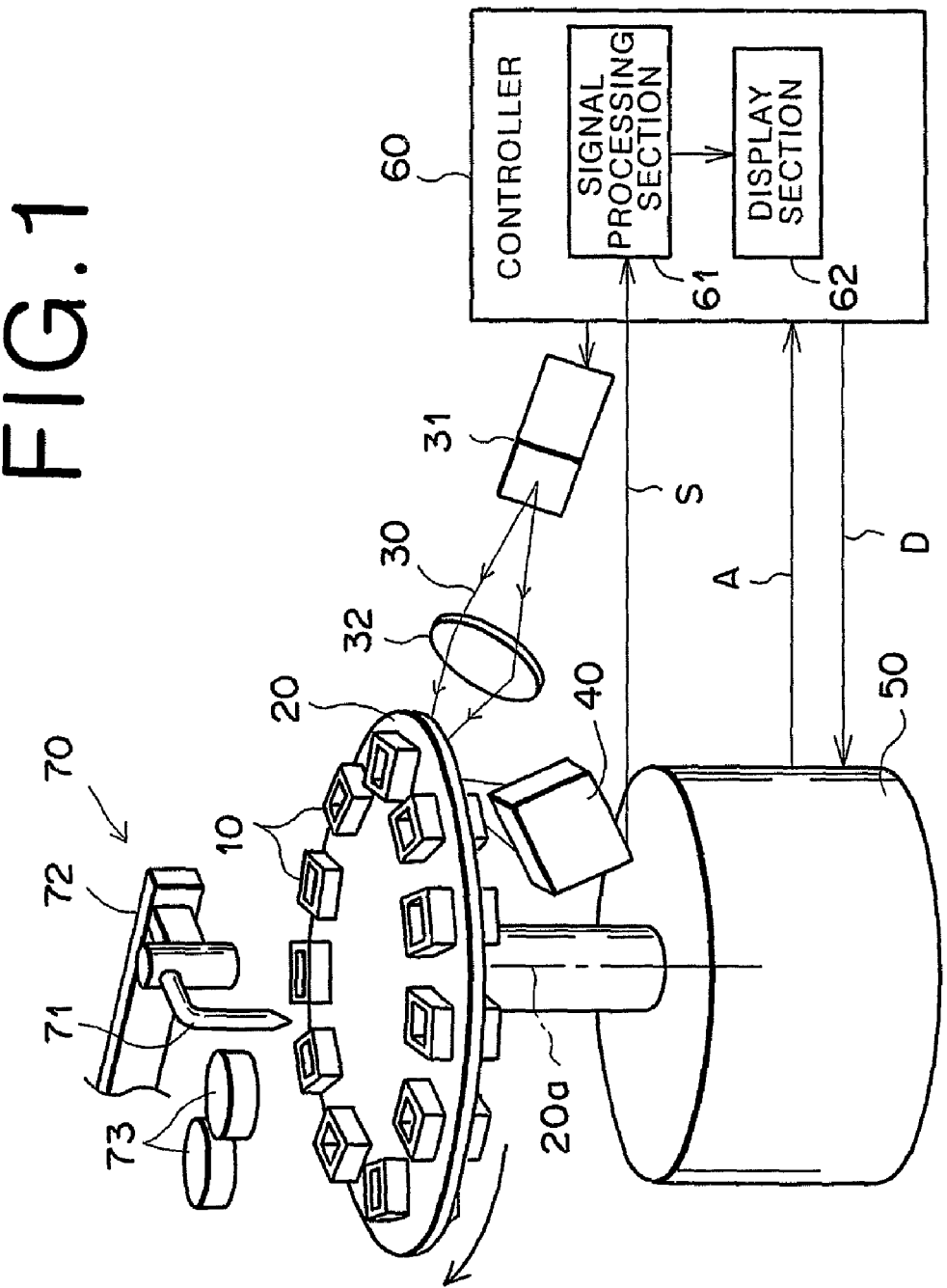
FIG. 1 is a perspective view showing a surface plasmon resonance measuring apparatus that employs surface plasmon resonance measuring chips constructed according to a first embodiment of the present invention.

As shown in FIG. 1, the surface plasmon resonance measuring apparatus has a turntable 20 for supporting a plurality of measuring chips 10; a laser light source (e.g., a semiconductor laser) 31 for emitting a measuring light beam (e.g., a laser beam) 30; a condenser lens 32 constituting an optical incidence system; a photodetector 40; supporting-body drive means 50 for rotating the above-mentioned turntable 20 intermittently; a controller 60 for controlling the supporting-body drive means 50 and also for receiving an output signal S from the photodetector 40 and performing a process which is to be described later; and an automatic sample supply mechanism 70.

Figure 2:
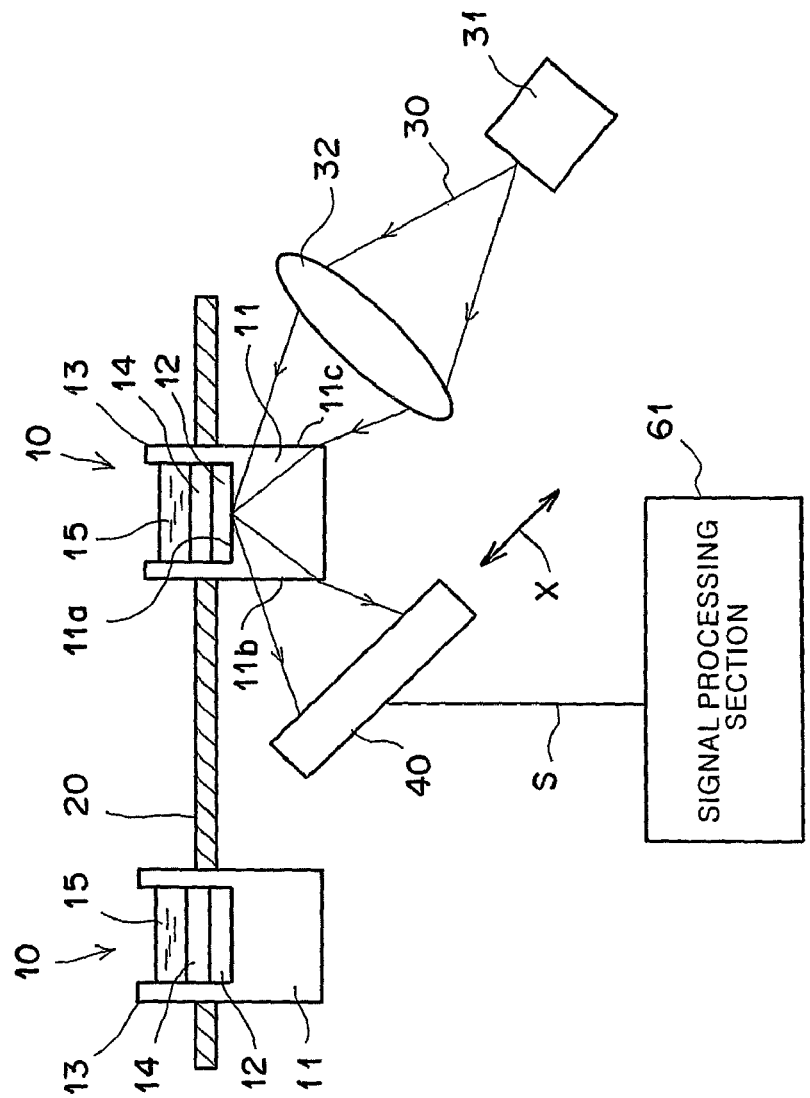
FIG. 2 is a partial-sectional side view showing the essential parts of the surface plasmon resonance measuring apparatus of FIG. 1.
Figure 3:
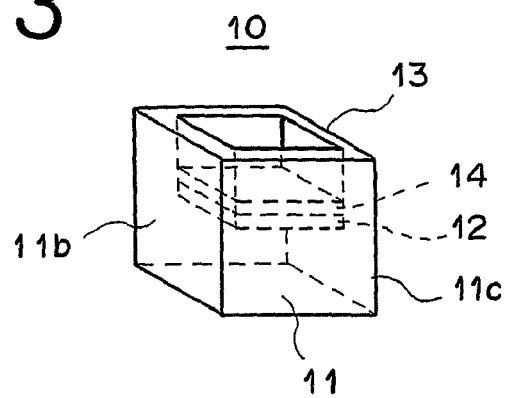
FIG. 3 is a perspective view showing the surface plasmon resonance measuring chip of the first embodiment of the present invention.

The measuring chip 10, as shown in FIGS. 2 and 3, is constructed of a transparent dielectric block 11 formed into the shape of a rectangular parallelepiped, for example; a metal film 12, formed on the top surface of the dielectric block 11, which consists of silver, copper, aluminum, etc.; and a sample holding frame 13 formed on the dielectric block 11 so that the metal film 12 is exposed to the outside. The dielectric block 11 is formed as a single block, which includes a top surface on which the metal film 12 is formed (top surface that constitutes an interface 11a to be described later), an entrance surface 11c that the light beam 30 enters, and an exit surface 11b from which the light beam 30 emerges. The sample holding frame 13 holds, for example, a liquid sample 15, as described later.

The dielectric block 11 and the sample holding frame 13, which constitute the measuring chip 10, are integrally formed, for example, from polymethylmethacrylate (PMMA), which is a transparent synthetic resin. The measuring chip 10 is exchangeable with respect to the turntable 20. To make the measuring chip 10 exchangeable, it is detachably fitted in a through hole formed in the turntable 20. In the first embodiment, a sensing medium 14 is mounted on the metal film 12. The sensing medium 14 will be described in detail later.

Note that it is desirable that the refractive index of the synthetic resin material of the dielectric block 11 generally be in a range of about 1.45 to 2.5. The reason for this is that a practical surface plasmon resonance angle is obtained in the refractive index range. It is further desirable to employ a synthetic resin in which a quantity of optical distortion (double refraction) is 20 to 420 nm. If a synthetic resin with such a small optical distortion is employed, measurements can be made with a high degree of accuracy. The quantity of optical distortion (double refraction) is measurable by a parallel nicol method.

The turntable 20 is constructed so that a plurality of measuring chips 10 are supported at equiangular intervals on a circle with respect to the axis of rotation 20a. The first embodiment employs 11 (eleven) measuring chips 10. The supporting-body drive means 50 is constructed of a stepping motor, etc., and is rotated intermittently at equiangular intervals equal to the pitch between the measuring chips 10.

The condenser lens 32, as shown in FIG. 2, collects and directs the light beam 30 toward the dielectric block 11. The light beam 30 enters the dielectric block 11 at the entrance surface 11c and converges at the interface 11a between the dielectric block 11 and the metal film 12 so that various angles of incidence are obtained. The incidence angle range includes an angle range where a total internal reflection condition for the light beam 30 is satisfied at the interface 11a, and where surface plasmon resonance is able to occur.

Note that the light beam 13 is p-polarized and caused to strike the interface 11a. For this reason, it is necessary to dispose the laser light source 31 so that the polarization direction thereof becomes a predetermined direction. Alternatively, the direction of polarization of the light beam 30 maybe controlled with a wavelength plate, a polarizing plate, etc.

The photodetector 40 is constructed of a line sensor consisting of a plurality of light-receiving elements arrayed in a row. The light-receiving elements are set along the direction of arrow X in FIG. 2.

The controller 60 receives an address signal A representing a position where rotation of the supporting-body drive means 50 is stopped, from the supporting-body drive means 50. This controller 60 also outputs a drive signal D to operate the supporting-body drive means 50, based on a predetermined sequence. The controller 60 is equipped with a signal processing section 60 for receiving the output signal S from the photodetector 40, and a display section 62 for receiving an output signal from the signal processing section 61.

The automatic sample supply mechanism 70 is constructed of a pipet 71 for suctioning and holding, for example, a predetermined amount of a liquid sample, and means 72 for moving the pipet 71. The automatic sample supply mechanism 70 suctions and holds a sample from a sample container 73 set at a predetermined place, and then supplies the sample to the sample holding frame 13 of the measuring chip 10 being stopped at a predetermined position.

A description will hereinafter be given of how a sample is analyzed by the surface plasmon resonance measuring apparatus constructed as described above. The turntable 21 is first rotated intermittently by the supporting-body drive means 50, as mentioned above. When the turntable 20 is stopped, a sample 15 is supplied by the automatic sample supply mechanism 70 to the sample holding frame 13 of the measuring chip 10 being at a predetermined position.

Thereafter, if the turntable 20 is rotated a few times and stopped, the measuring chip 10 holding the sample 15 in the sample holding frame 13 is located at a measuring position (the position of the measuring chip 10 on the right in FIG. 2) where the light beam 30 enters the dielectric block 11. If the measuring chip 10 is held at the measuring position, the laser light source 31 is driven in response to an output signal from the controller 60. Then, the light beam 30 emitted from the laser light source 31 is collected and directed to the dielectric block 11 by the condenser lens 32 and converges at the interface 11a between the dielectric block 11 and the metal film 12. The light beam 30 satisfying total internal reflection at the interface 11a is detected by the photodetector 40.

Since it enters the dielectric block 11 and converges at the interface 11a, the light beam 30 contains components incident on the interface 11a at various incidence angles θ. Note that these incidence angles θ are equal to or greater than a critical angle at which total internal reflection occurs. Therefore, the light beam 30 satisfies total internal reflection at the interface 11a, and the reflected light beam 30 contains components reflected at various angles of reflection. The optical system, which includes the condenser lens 32, etc., may be constructed so that the light beam 30 is defocused when it strikes the interface 11a. If done in this manner, errors in the measurement of surface plasmon resonance (e.g., errors in the measurement of the position of the dark line) are averaged and therefore accuracy of measurement is enhanced.

Figure 4:
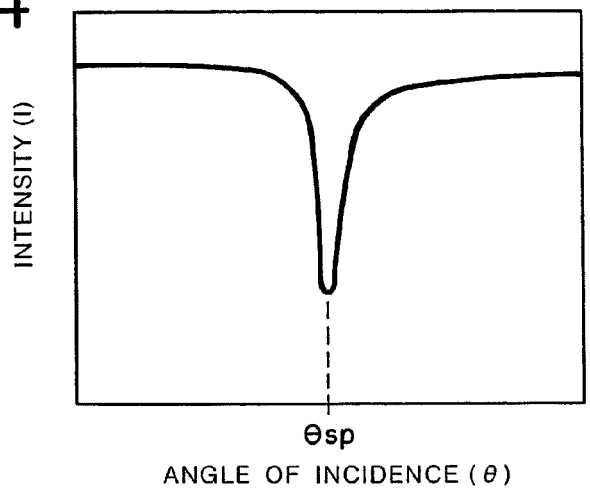
FIG. 4 is a graph showing the relationship between the incidence angle at which a light beam enters the surface plasmon resonance measuring chip, and the intensity of the light beam reflected at the measuring chip.

When the light beam 30 satisfies total internal reflection at the interface 11a, as described above, an evanescent wave propagates on the side of the metal film 12 through the interface 11a. And when the light beam 30 strikes the interface 11a at a specific incidence angle $\theta_{sp}$, the evanescent wave resonates with the surface plasmon excited at the surface of the metal film 12. Because of this, the intensity I of the light reflected at the interface 11a drops sharply. The relationship between the specific incidence angle $\theta_{sp}$ and the intensity I is shown in FIG. 4.

Hence, the quantity of light detected by each light-receiving element is calculated from the light-quantity detection signal S output from the photodetector 40. Based on the position of the light-receiving element that detected a dark line, the specific incidence angle $\theta_{sp}$ (at which ATR occurs) is calculated. And based on a curve for the relationship between the intensity I and the incidence angle $\theta_{sp}$, a specific substance in the sample 15 can be quantitatively analyzed. The signal processing section 61 of the controller 60 quantitatively analyzes a specific substance in the sample 15, based on the principle described above. The result of analysis is displayed on the display section 62.

In the case where a single measurement is made on a single sample 15, the measurement is completed in the manner described above. The measuring chip 10 for which measurement has been finished is removed from the turntable 20 by hand or with automatic removal means. On the other hand, in the case where a plurality of measurements are made on a single sample 15, the measuring chip 10 remains held in the turntable 20 after the first measurement. After one revolution of the turntable 20, the sample 15 held in the measuring chip 10 may be measured again.

In the surface plasmon resonance measuring apparatus, as described above, a plurality of measuring chips 10 are supported by the turntable 20 and are sequentially located at the measuring position by moving the turntable 20. Therefore, the samples 15 held in the sample holding frames 13 of the measuring chips 10 can be successively measured by movement of the turntable 20. Thus, according to the surface plasmon resonance measuring apparatus of the first embodiment, it becomes possible to measure a great number of samples 15 in a short period of time.

The surface plasmon resonance measuring apparatus of the first embodiment is provided with the automatic sample supply mechanism 70, whereby the time required to supply a sample is also shortened. Thus, it becomes possible to measure a great number of samples 15 in an even shorter period of time.

In the first embodiment, the dielectric block 11, the metal film 12, and the sample holding frame 13 are formed integrally with one another and constitute the measuring chip 10.

The measuring chip 10 is made exchangeable with respect to the turntable 20. Therefore, if the measuring chips 10, holding the samples 15 for which measurement has been completed, are removed from the turntable 20, and new measuring chips 10 are supported by the turntable 20, the new measuring chips 10 can be successively measured. Thus, it becomes possible to measure a great number of samples 15 in an even shorter period of time.

In the measuring chip 10 according to the first embodiment, the optical coupling of the dielectric block 11 with another dielectric block through an index-matching solution is not needed as in the prior art. Thus, the measuring chip 10 of the first embodiment is easy to handle and does not require an index-matching solution that would have a detrimental influence on the environment.

Note that the sensing medium 14 being mounted on the surface of the metal film 12 couples with a specific substance in the sample 15. As a combination of the specific substance and the sensing medium 14, there is, for example, a combination of an antigen and an antibody. In that case, an antigen-antibody reaction can be detected, based on the angle $\theta_{sp}$ at which ATR occurs.

As previously stated, it is necessary that the light beam 30 be p-polarized and strike the interface 11a. Because of this, the laser light source 31 is disposed so that the polarization direction thereof becomes a predetermined direction, or the polarization direction of the light beam 30 is controlled with a wavelength plate or polarizing plate. However, in the case where the dielectric block 11 consists of synthetic resin, there are cases where a strong s-polarized component occurs due to optical distortion (e.g., double refraction, etc.) when the light beam 30 reaches the interface 11a. In those cases, the S/N ratio for the light-quantity detection signal S output from the photodetector 40 is reduced and accuracy of measurement deteriorates.

However, in the first embodiment, the transparent dielectric block 11 is formed from PMMA, and in the case of PMMA, the intensity of the s-polarized component is on the order of a few percent of the intensity of the light beam 30 at the interface 11a and is therefore reduced to 50 percent or less. In this case, there is no practical hindrance in a general sample analysis that is made with the surface plasmon resonance measuring apparatus of the first embodiment.

In the case where the coupling reaction between a specific substance in the sample 15 and the sensing medium 14 is examined when they are an antigen and an antibody, the intensity of the s-polarized component at the interface 11a must generally be 30 percent or less of the intensity of the light beam 30 at the interface 11a. Particularly, in the case where the result of analysis is utilized in pharmaceutical manufacture, it must be 10 percent or less. In the case where the dielectric block 11 is formed from PMMA, these requirements are satisfied.

Note that it is difficult to suppress the intensity of the s-polarized component (conversion ratio R) to less than or equal to 50%, less than or equal to 30%, or less than or equal to 10% simply by employing PMMA as the material for the dielectric block 11. These conversion ratios R can be realized by applying the method of manufacture of a surface plasmon resonance measuring chip of the present invention, when PMMA is employed. An embodiment of this method will be described in detail below.

Figure 5:
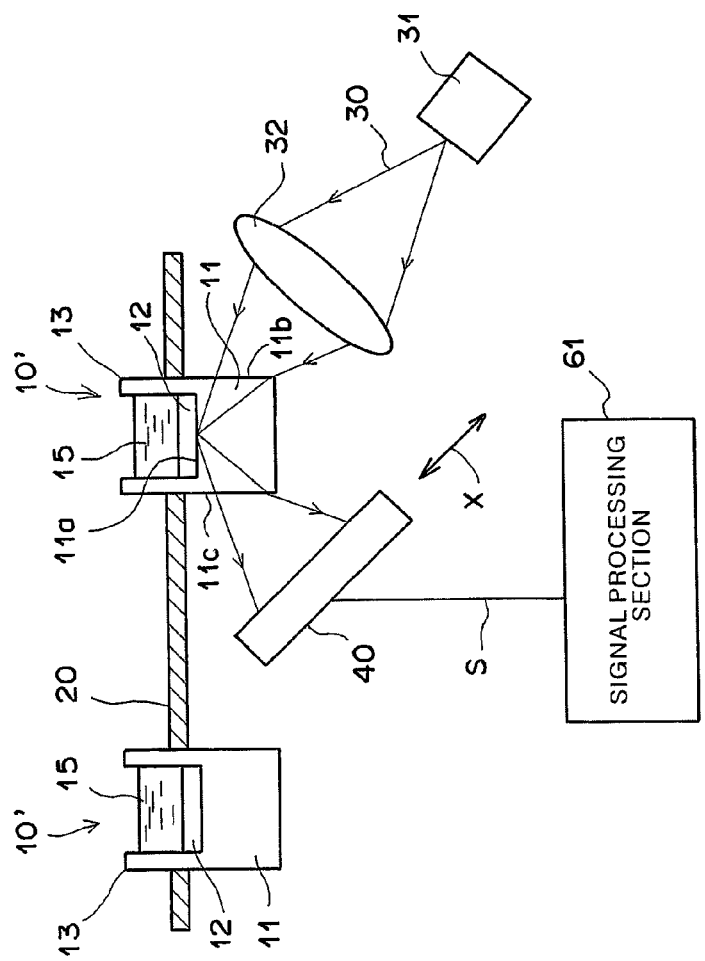
FIG. 5 is a partial-sectional side view showing the surface plasmon resonance measuring apparatus that employs surface plasmon resonance measuring chips constructed according to a second embodiment of the present invention.

FIG. 5 shows a surface plasmon resonance measuring chip 10' constructed according to a second embodiment of the present invention. Note in the figure that the same reference numerals are applied to the same parts as those in FIG. 2, and that a description thereof will not be given unless particularly necessary (the same applies to the following description).

The measuring chip 10' of the second embodiment differs from the measuring chip 10 shown in FIGS. 2 and 3 only in that the sensing medium 14 is not used. Therefore, in the second embodiment, a substance in a sample 15 is quantitatively analyzed without coupling between a specific substance in the sample 15 and the sensing medium 14.

Other than the above-mentioned point, the measuring chip 10' has the same construction as the measuring chip 10 shown in FIGS. 2 and 3, including that a transparent dielectric block 11 is formed from PMMA. Therefore, in the case of the measuring chip 10', the same effect as the case of the measuring chip 10 can be obtained.

Figure 6:
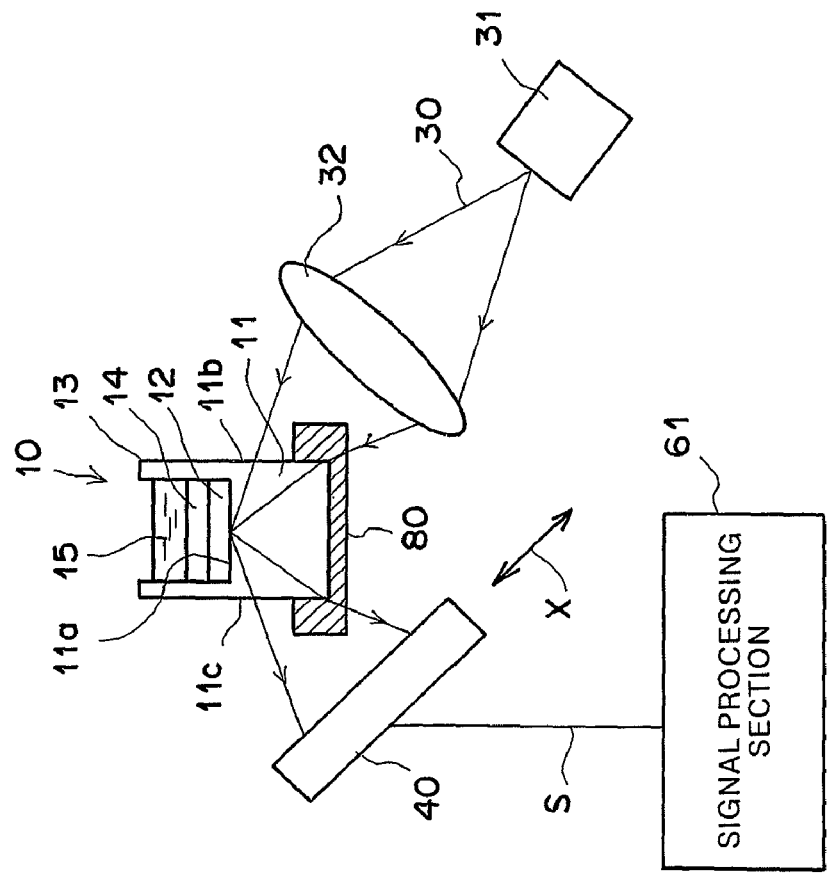
FIG. 6 is a partial-sectional side view showing another surface plasmon resonance measuring apparatus that employs the surface plasmon resonance measuring chip of the present invention.

It has been described that the measuring chip is automatically supplied by the turntable 20 to the measuring position where the light beam is irradiated to the measuring chip, and is automatically removed from the turntable 20. However, the measuring chip of the present invention can be used in a surface plasmon resonance measuring apparatus that does not perform such automatic supply and removal. In a surface plasmon resonance measuring apparatus shown in FIG. 6, for instance, an attachment 80 is fixed with respect to a laser light source 31, a condenser lens 32, and a photodetector 40. In this type of apparatus, a measuring chip 10 is manually installed in the attachment 80 as a measurement is made, and is manually removed from the attachment 80 after measurement.

The surface plasmon resonance measuring chip of the present invention can be formed into shapes other than the aforementioned shape. In FIGS. 7 to 12 there are shown surface plasmon resonance measuring chips in accordance with other embodiments of the present invention.

Figure 7:
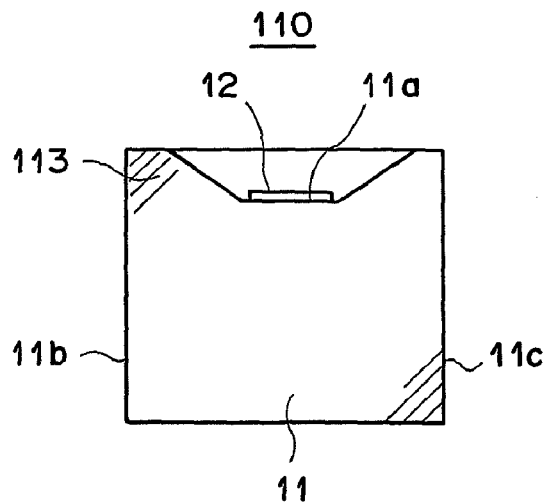
FIG. 7 is a sectional side view showing a surface plasmon resonance measuring chip constructed according to a third embodiment of the present invention.

FIG. 7 shows a measuring chip 110 constructed according to a third embodiment of the present invention. Compared with the measuring chip 10 shown in FIG. 3, the portion of a dielectric block 11 is the same in shape, but the portion of a sample holding frame 113 differs in shape. That is, the sample holding frame 113 has a recess whose cross section gradually increases in size from the bottom thereof toward the top. A metal film 12 is generally formed on the dielectric block 11 by vapor deposition. If the sample holding frame 113 is formed into a shape such as that described above, a deposited metal film (metal film 12) is blocked by the sample holding frame, and therefore can be prevented from becoming uneven in thickness. In the measuring chip 110 of the third embodiment, as with the aforementioned embodiments, the transparent dielectric block 11 is formed from PMMA. Therefore, the third embodiment is capable of obtaining the same effect as the aforementioned effect.

Figure 8:
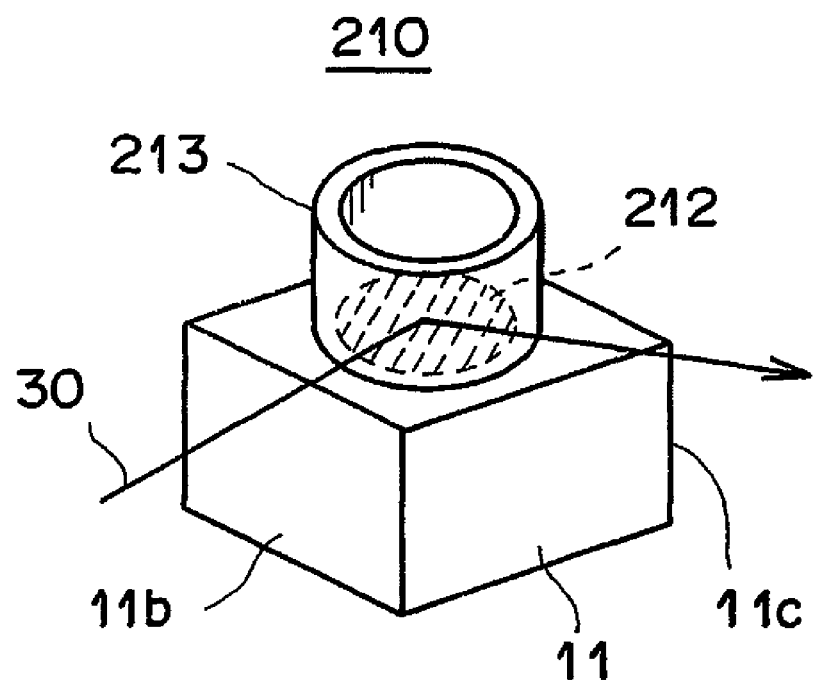
FIG. 8 is a perspective view showing a surface plasmon resonance measuring chip constructed according to a fourth embodiment of the present invention.

FIG. 8 shows a measuring chip 210 constructed according to a fourth embodiment of the present invention. Compared with the measuring chip 10 shown in FIG. 3, the portion of a dielectric block 11 is the same in shape, but the portion of a sample holding frame 213 is formed into a cylindrical shape. A metal film 12 is likewise formed into a circular shape according to the shape of the sampling holding frame 213. As with the aforementioned embodiments, the transparent dielectric block 11 is formed from PMMA. Therefore, the measuring chip 210 of the fourth embodiment can likewise obtain the same effect as the aforementioned effect.

Figure 9:
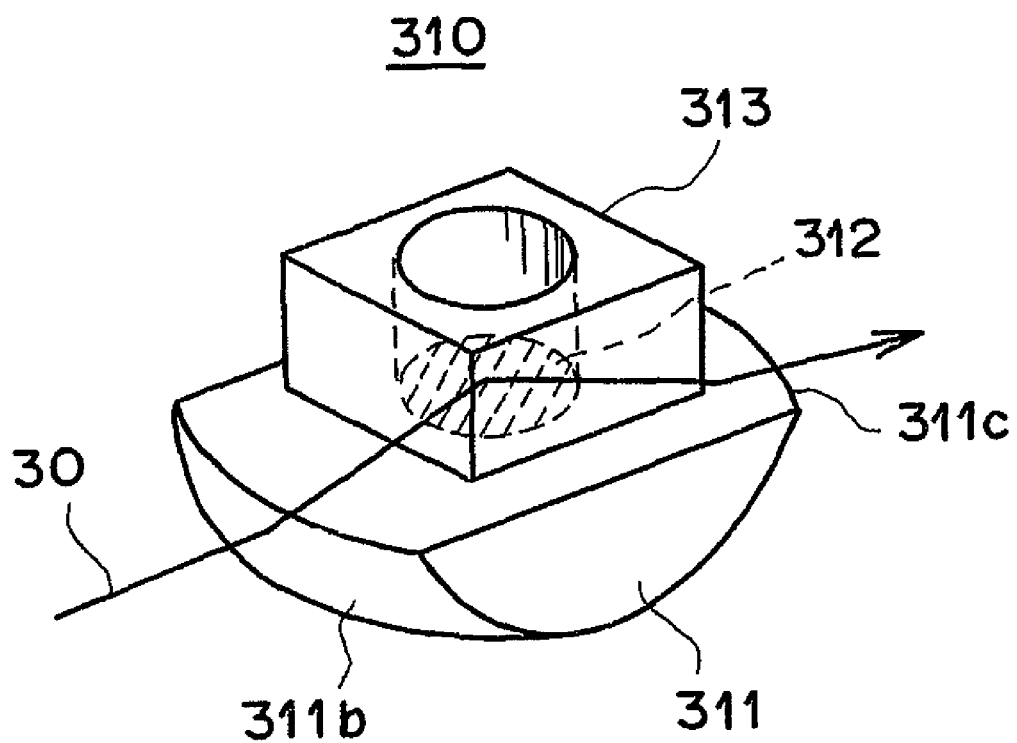
FIG. 9 is a perspective view showing a surface plasmon resonance measuring chip constructed according to a fifth embodiment of the present invention.

FIG. 9 shows a measuring chip 310 constructed according to a fifth embodiment of the present invention. A sample holding frame 313 has a cylindrical hole. A metal film 312 is likewise formed into a circular shape according to the shape of the sample holding frame 313. Furthermore, a dielectric block 311 has a light entrance surface 311b and a light exit surface 311c, which are formed by a portion of a spherical surface. If the dielectric block 311 is formed like this, the block 311 has a lens effect at the light entrance surface 311b and the light exit surface 311c with respect to a light beam 30. As with the aforementioned embodiments, the transparent dielectric block 311 is formed from PMMA. Therefore, the measuring chip 310 of the fifth embodiment can likewise obtain the same effect as the aforementioned effect.

Figure 10:
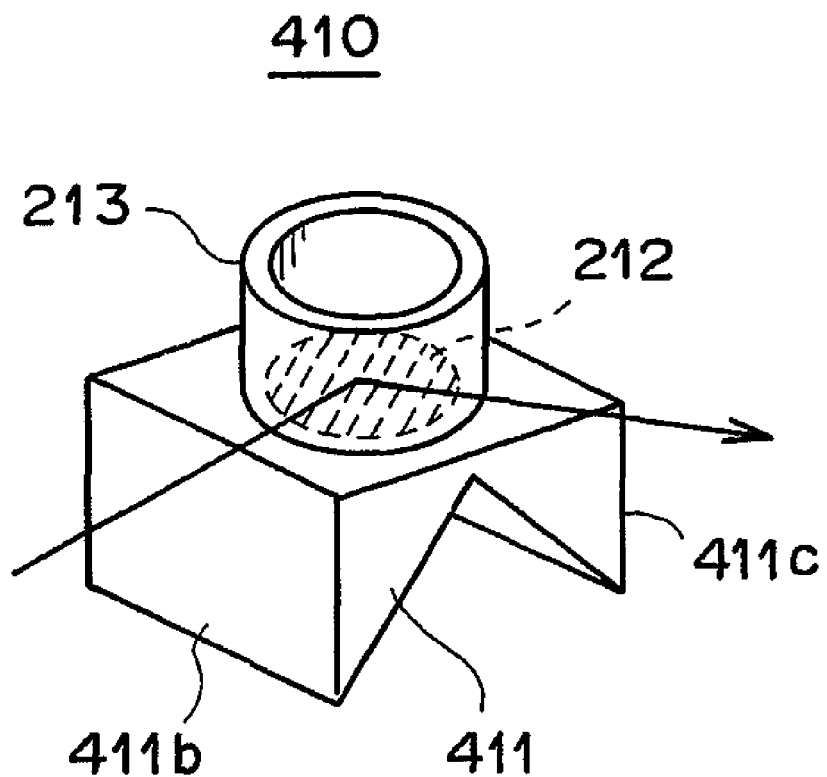
FIG. 10 is a perspective view showing a surface plasmon resonance measuring chip constructed according to a sixth embodiment of the present invention.

FIG. 10 shows a measuring chip 410 constructed according to a sixth embodiment of the present invention. Compared with the measuring chip 210 shown in FIG. 8, the portion of a dielectric block 411 differs in shape. As shown in FIG. 10, a portion through which a light beam 30 does not pass is cut out from the dielectric block 411. If the dielectric block 411 has such a shape, the amount of material (e.g., the aforementioned glass, transparent synthetic resin, etc.) that is used can be saved. As with the aforementioned embodiments, the transparent dielectric block 411 is formed from PMMA. Therefore, the measuring chip 410 of the sixth embodiment can likewise obtain the same effect as the aforementioned effect.

Figure 11:
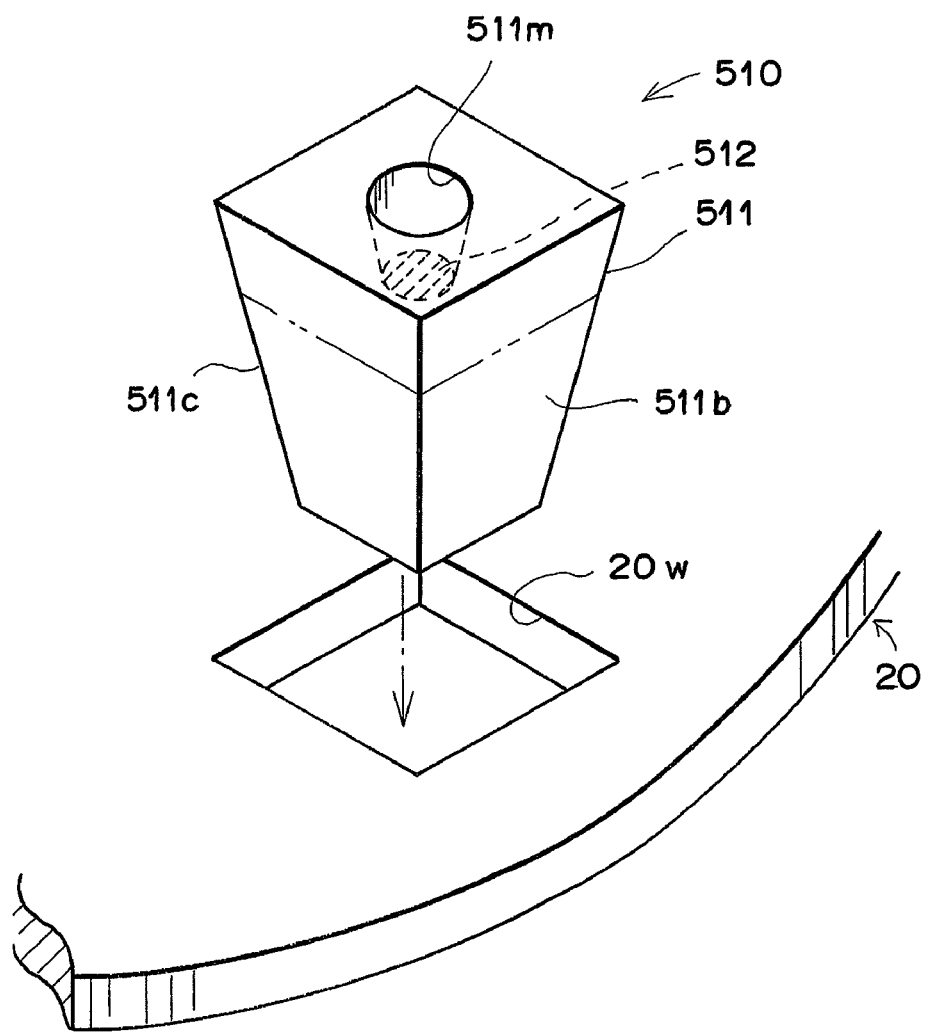
FIG. 11 is a perspective view showing a surface plasmon resonance measuring chip constructed according to a seventh embodiment of the present invention.

FIG. 11 shows a surface plasmon resonance measuring chip 510 constructed according to a seventh embodiment of the present invention. The measuring chip 510 consists of a dielectric block 511, which is formed, for example, from the aforementioned transparent synthetic resin. As shown in FIG. 11, the dielectric block 511 is formed by a portion of a generally quadrangular pyramid. More specifically, it is formed by the upper portion of an inverted quadrangular pyramid. That is, the dielectric block 511 has a cross section that gradually increases in size toward the top thereof.

Two side surfaces of the four side surfaces of the dielectric block 511 are used as a light entrance surface 511b and a light exit surface 511b, respectively. The entrance surface 511b and the exit surface 511b may be transparent, or only a region through which a light beam passes may be transparent. The remaining two side surfaces may be transparent like the entrance and exit surfaces 511b, 511c, or may be semitransparent.

The dielectric block 511 is also provided with a sample holding hole 511m having a circular cross section, which gradually increases in diameter toward the top surface of the dielectric block 511. The bottom surface of the sample holding hole 511m is provided with a metal film 512. That is, in the seventh embodiment, the portion of the dielectric block 511 which forms the side wall portion and bottom portion of the sample holding hole 511m constitutes a sample holding frame.

As shown in FIG. 11, the turntable 20 (see FIG. 1) of a surface plasmon resonance measuring apparatus employing the surface plasmon resonance measuring chip 510 of the seventh embodiment has a square chip holding bore 20w. The cross section of the chip holding bore 20w conforms to that of the dielectric block 511 so that it can receive the dielectric block 511. That is, the cross section of the chip holding bore 20w is tapered, gradually increasing in size from the bottom thereof toward the top.

The surface plasmon resonance measuring chip 510 is fitted in the chip holding bore 20w and is held in the turntable 20. Thus, if the square chip holding bore 20w and the square cross-section dielectric block 511 engage with each other, the dielectric block 511 is automatically set in a predetermined direction within a horizontal plane parallel to the surface of the turntable 20, and there is no possibility that the dielectric block 511 will be shifted horizontally from the sample holding bore 20w. Thus, the surface plasmon resonance measuring chip 510 of the seventh embodiment can be very easily positioned within a horizontal plane.

In addition, if the dielectric block 511 with inclined side surfaces is inserted into the chip holding bore 20w, the dielectric block 511 is stopped and held at a height where the inclined surfaces of the dielectric block 511 and the chip holding bore 20w engage with each other, and consequently, the dielectric block 511 can be very easily positioned in the vertical direction thereof. In the seventh embodiment, when the measuring chip 510 is positioned in the vertical direction, the portion of the dielectric block 511 below the broken line shown in FIG. 11 protrudes downward from the turntable 20. As with the aforementioned embodiments, the transparent dielectric block 511 is formed from PMMA. Therefore, the measuring chip 510 of the seventh embodiment can likewise obtain the same effect as the aforementioned effect.

FIGS. 12A and 12B show a surface plasmon resonance measuring chip 610 constructed according to an eighth embodiment of the present invention. The surface plasmon resonance measuring chip 610 differs from the measuring chip 510 shown in FIG. 11 in that a sample holding frame 613 is formed on a dielectric block 611. The sample holding frame 613 is formed integrally with the dielectric block 611. The sample holding frame 613 is formed from a portion of a cone and provided with a sample holding hole 613a having a cross section that gradually increases in diameter from the bottom thereof toward the top. A metal film 612 is formed on the bottom of the sample holding hole 613a.

The dielectric block 611 has a shape similar to the dielectric block 511 shown in FIG. 11. Two side surfaces of the 4 side surfaces of the dielectric block 611 are used as a light entrance surface 611b and a light exit surface 611c, respectively. Because the dielectric block 611 is formed into such a shape, horizontal positioning and vertical positioning can be easily performed in the case where the surface plasmon resonance measuring chip 610 of the eighth embodiment is fitted and held in the chip holding bore 20w of the turntable 20 shown in FIG. 11. As with the aforementioned embodiments, the transparent dielectric block 611 is formed from PMMA. Therefore, the measuring chip 610 of the eighth embodiment can likewise obtain the same effect as the aforementioned effect.

While it has been described in the aforementioned embodiments that the dielectric blocks are formed from PMMA, the material of the dielectric blocks is not limited to PMMA. For example, even if "ZEONEX 330R", a cycloolefin polymer manufactured by Japan Zeon, is employed, nearly the same effect as the case of PMMA can be obtained.

Further, synthetic resins such as "ZEONOR", a cycloolefin polymer manufactured by Japan Zeon, and "ABERU", an ethylene tetracyclododecene cycloolefin polymer manufactured by Mitsui Chemical, may also be employed as the material for the dielectric block. If the aforementioned synthetic resins are viewed from the point of suppressing the conversion ratio R from the p-polarized component to the s-polarized component, then "ZEONEX 330R", "ZEONOR", and "ABERU" are more preferable than PMMA.

Figure 16:
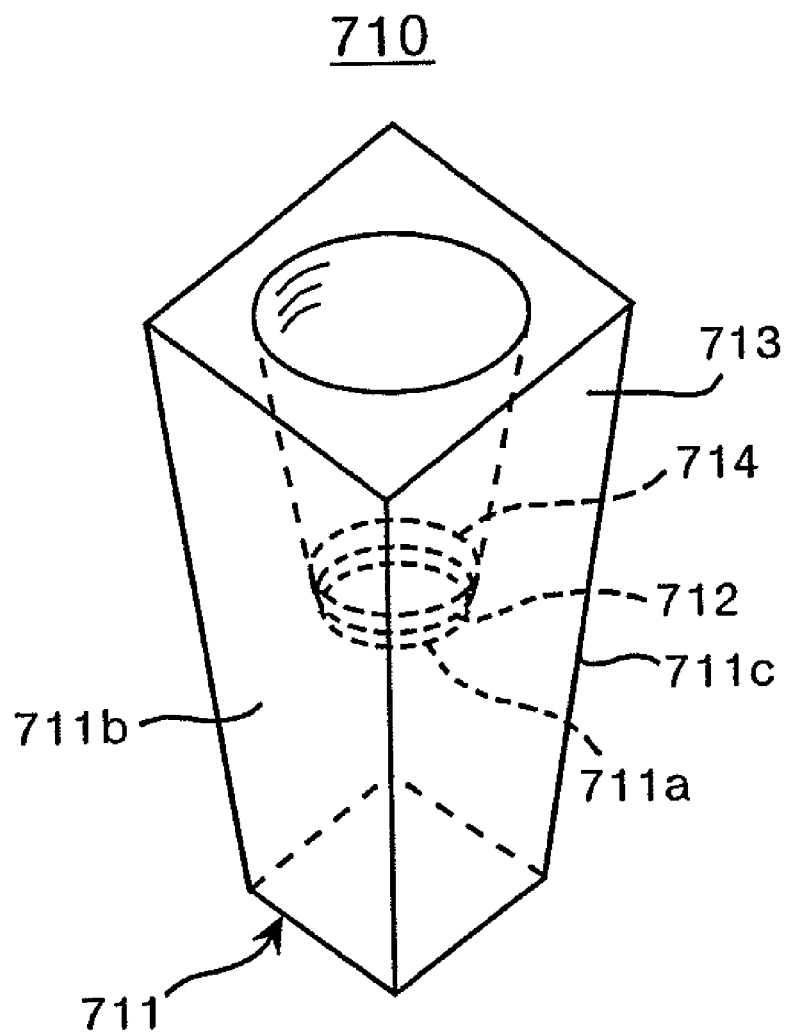
FIG. 16 is a perspective view showing an example of a surface plasmon resonance measuring chip manufactured according to the method of the present invention.

Next, an embodiment of the method of manufacture of a surface plasmon resonance measuring chip according to the present invention will be described. Note that a case will be described in which a measuring chip 710 of a shape as shown in FIG. 16 will be described. As shown in the figure, the measuring chip 710 is constructed of a transparent dielectric block 711 formed into the shape of a section of a rectangular cone, for example; a metal film 712, formed on a surface 711a of the dielectric block 711, which consists of gold, silver, copper, aluminum, etc.; and a sample holding frame 713 formed on the dielectric block 711 above the metal film 712 to create a space having its lateral surfaces closed. The dielectric block 711 is formed as a single block, which includes the surface 711a on which the metal film 712 is formed, an entrance surface 711b that the measurement light beam enters, and an exit surface 711c from which the light beam exits. The sample holding frame 713 composes a space for holding liquid, and the space holds, for example, a liquid sample.

Figure 17:
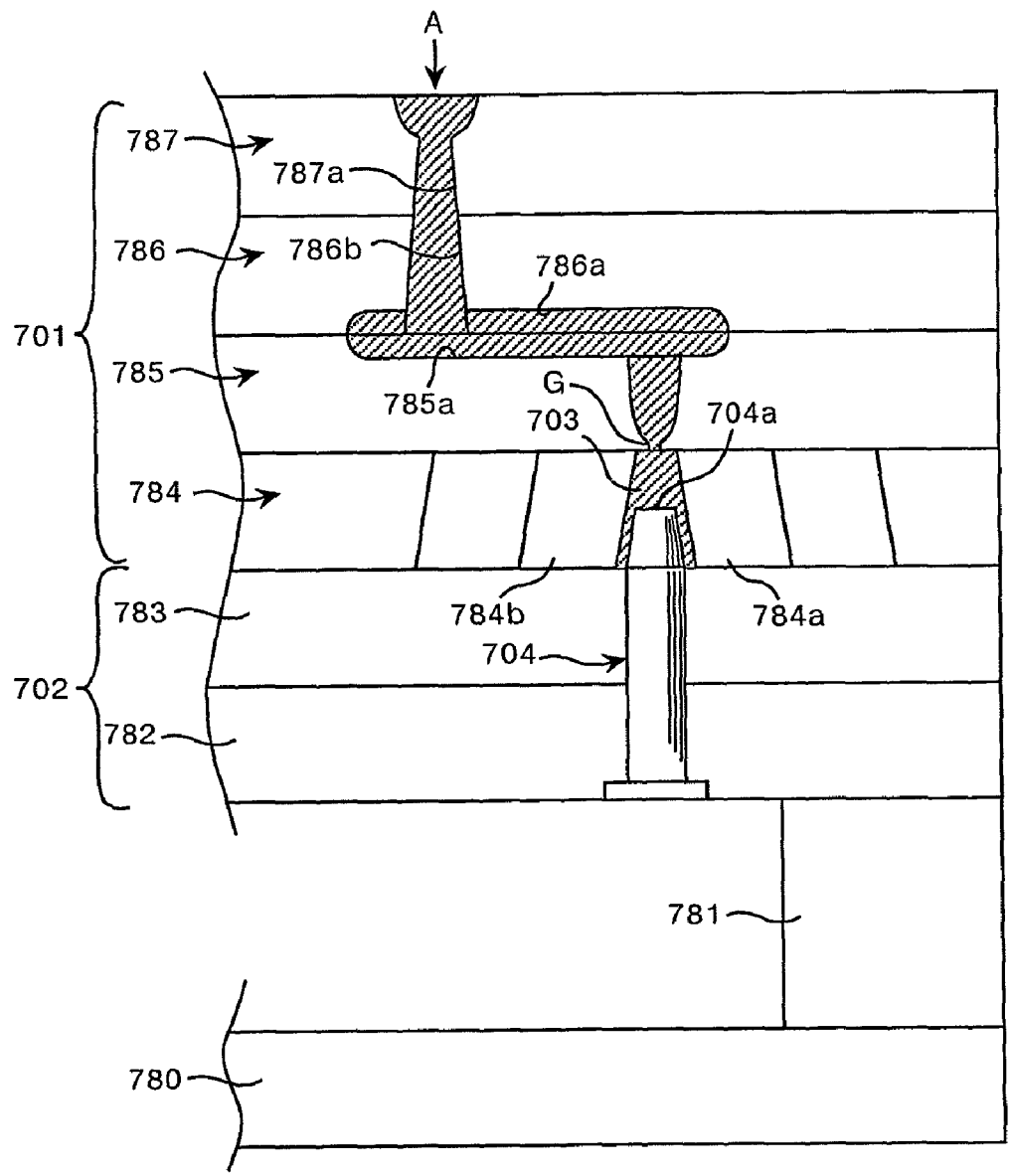
FIG. 17 is a sectional side view of an example of an apparatus for manufacturing a surface plasmon resonance measuring chip according to the method of the present invention.

FIG. 17 schematically shows an injection molding apparatus for manufacturing a measuring chip by an embodiment of a method of manufacture according to the present invention. As shown in the figure, this injection molding apparatus is constructed of a lower mold 702; fixed to a movable attachment board 780, which is vertically movable; via a spacer block 781; and an upper mold 701 that closely contacts with and separates from the lower mold 702.

The lower mold 702 is constructed of a receiving board 782; a stopper plate 783 assembled above the receiving board 782; and a pin 704 that protrudes towards the upper mold 701. The upper mold is constructed of a movable board 784 that comes into close contact with the lower mold 702 in the vertical direction when the lower mold 702 presses against it from below; a runner plate 785; a runner stripper plate 786; and a fixed attachment board 787. The vertical position of the fixed attachment board is fixed. When the lower mold 702 drops a predetermined distance from the position shown in FIG. 17, the movable board 784, the runner plate 785, and the runner stripper plate 786 separate therefrom while separating from each other.

Two slider blocks 784a and 784b, that move in the direction which is horizontal in the figure and create a space 703 therebetween when in a state of close contact, are built into movable board 784. When the upper mold 701 and the lower mold 702 are placed in close contact, the tip of the pin 704 protrudes within the space 703. Note that in FIG. 17, the space through which molten synthetic resin flows, such as the space 703, is indicated by hatching.

Runner grooves 785a and 786a are formed on the upper surface of runner plate 785 and the lower surface of runner stripper plate 786, respectively, so that they align when the runner plate 785 and the runner stripper plate 786 are placed in close contact. In addition, a resin introducing channel 786b that communicates with the runner groove 786a is formed in the runner stripper plate 786. Further, a resin introducing channel 787a, that communicates with the resin introducing channel 786b when the fixed attachment board 787 is placed in close contact with the runner stripper plate 786, is formed in the fixed attachment board 787.

When transparent synthetic resin is forced through the resin introducing channel 787a of fixed attachment board 787 in the direction indicated by the arrow A, with the upper mold 701 and the lower mold 702 in a state of close contact as shown in FIG. 17, the synthetic resin is injected into the space 703 from pin gate G. If the upper mold 701 and the lower mold 702 are separated after the synthetic resin cools and solidifies, a dielectric block 711 that constitutes the measuring chip 710 shown in FIG. 16 can be obtained.

When injection molding the dielectric block 711 in this manner, the gate G is positioned at a position that faces a tip surface 704a of the pin, which is the mold surface that defines the surface 711a of the dielectric block 711. Thus, the reduction in the strength of the dielectric block at the merge points of the synthetic resin's flow and the generation of welds (lines occurring at the merge plane of synthetic resin flow) at the surface 711a of the dielectric block 711 are prevented.

Figure 18:
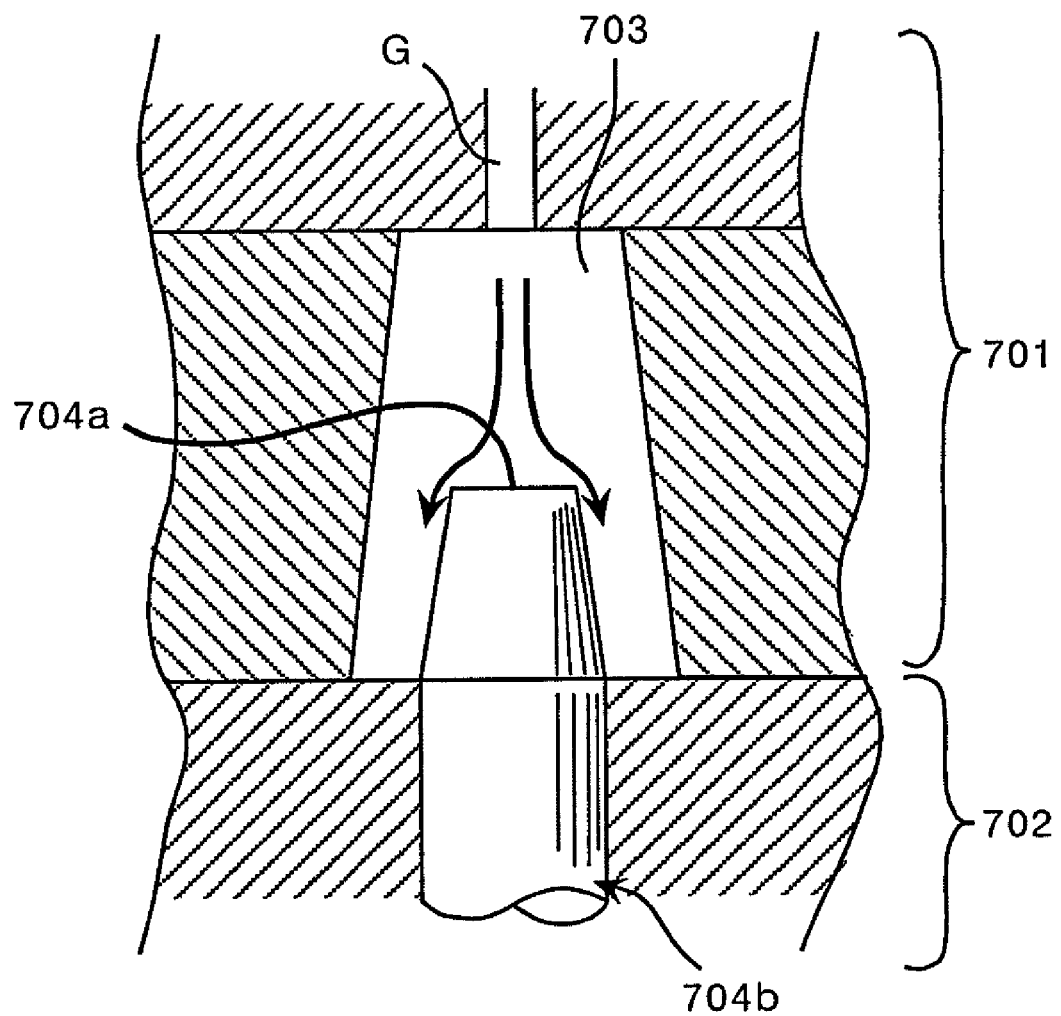
FIG. 18 is a magnified sectional side view of the main parts of the apparatus of FIG. 17.

That is, at this time, the synthetic resin flows towards the tip surface 704a of the pin 704, as indicated by the two arrows in FIG. 18, which is a magnified view of the area surrounding the pin 704. Thus, the flow of synthetic resin does not merge at the surface 711a (see FIG. 16) of the dielectric block 711. By preventing the generation of welds in this manner, it becomes possible to suppress the intensity of the s-polarized component (conversion ratio R) of the light beam incident on the surface 711a of dielectric block 711 to the aforementioned less than or equal to 50%, less than or equal to 30%, or less than or equal to 10%.

After injection molding the dielectric block 711 as described above, if a metal film 712 is formed on the surface 711a thereof, and further fixing a sensing medium 714 on the metal film 712, the measuring chip 710 as shown in FIG. 16 is obtained.

Note that the method of manufacture of a measuring chip according to the present invention is not limited to a case in which a dielectric block 711 of a shape described above is injection molded. The method is applicable to cases in which dielectric blocks of other shapes are injection molded, and exhibits similar effects. Further, the gate G is not limited to the pin gate described above, and may be a gate of other forms, such as a fan gate or the like.

Although the present invention has been described with reference to the preferred embodiments thereof, the invention is not to be limited to the details given herein, but may be modified within the scope of the invention hereinafter claimed.

What is claimed is:

1. A surface plasmon resonance measuring chip for use in a surface plasmon resonance measurement apparatus constituted of a light source for emitting a light beam; an optical system for making said light beam enter a dielectric block at various angles of incidence so that a condition for total internal reflection is satisfied at an interface between said dielectric block and a metal film; and
   photodetection means for detecting the intensity of said light beam satisfying total internal reflection at said interface to detect surface plasmon resonance; comprising:
   a dielectric block;
   a metal film, formed on a surface of said dielectric block, for placing a sample thereon;
   wherein said dielectric block is formed as a single block that includes an entrance surface which said light beam enters, an exit surface from which said light beam emerges, and a surface on which said metal film is formed;
   said metal film is united with said dielectric block;
   said dielectric block is formed from a synthetic resin in which, when said light beam is p-polarized outside said dielectric block and then strikes said interface, the intensity of an s-polarized component at said interface is 50% or less of the intensity of said light beam at said interface; and
   said dielectric block has a cut out portion in a region where said light beam does not penetrate.

2. The surface plasmon resonance measuring chip as set forth in claim 1, wherein said dielectric block is formed from a synthetic resin in which, when said light beam is p-polarized outside said dielectric block and then strikes said interface, the intensity of a s-polarized component at said interface is 30% or less of the intensity of said light beam at said interface.

3. The surface plasmon resonance measuring chip as set forth in claim 1, wherein said dielectric block is formed from a synthetic resin in which, when said light beam is p-polarized outside said dielectric block and then strikes said interface, the intensity of a s-polarized component at said interface is 10% or less of the intensity of said light beam at said interface.

4. The surface plasmon resonance measuring chip as set forth in claim 1, wherein said synthetic resin is a synthetic resin that is selected from polymethylmethacrylate, a cycloolefin polymer, or a cycloolefin copolymer.

5. A surface plasmon resonance measuring chip for use in a surface plasmon resonance measurement apparatus constituted of a light source for emitting a light beam; an optical system for making said light beam enter a dielectric block at various angles of incidence so that a condition for total internal reflection is satisfied at an interface between said dielectric block and a metal film; and
   photodetection means for detecting the intensity of said light beam satisfying total internal reflection at said interface to detect surface plasmon resonance; comprising:
   a dielectric block;
   a metal film, formed on a surface of said dielectric block, for placing a sample thereon;
   wherein said dielectric block is formed as a single block that includes an entrance surface which said light beam enters, an exit surface from which said light beam emerges, and a surface on which said metal film is formed;
   said metal film is united with said dielectric block;
   said dielectric block is formed from a synthetic resin in which, when said light beam is p-polarized outside said dielectric block and then strikes said interface, the intensity of an s-polarized component at said interface is 50% or less of the intensity of said light beam at said interface;
   said dielectric block is formed in a quadrangular pyramid shape;
   said dielectric block comprises a sample holding hole having a circular cross section which gradually increases in diameter toward a top surface of said dielectric block; and
   a bottom surface of said dielectric block is contiguous to said metal film.

6. The surface plasmon resonance measuring chip as set forth in claim 5, wherein said dielectric block is formed from a synthetic resin in which, when said light beam is p-polarized outside said dielectric block and then strikes said interface, the intensity of a s-polarized component at said interface is 30% or less of the intensity of said light beam at said interface.

7. The surface plasmon resonance measuring chip as set forth in claim 5, wherein said dielectric block is formed from a synthetic resin in which, when said light beam is p-polarized outside said dielectric block and then strikes said interface, the intensity of a s-polarized component at said interface is 10% or less of the intensity of said light beam at said interface.

8. The surface plasmon resonance measuring chip as set forth in claim 5, wherein said synthetic resin is a synthetic resin that is selected from polymethylmethacrylate, a cycloolefin polymer, or a cycloolefin copolymer.

* * * * *